United States Patent
Joensuu et al.

(10) Patent No.: US 9,133,494 B2
(45) Date of Patent: Sep. 15, 2015

(54) IMPROVING THE PRODUCTION OF FOREIGN PROTEINS

(75) Inventors: Jussi Joensuu, VTT (FI); Eero Mustalahti, VTT (FI); Andrew Conley, Espoo (FI)

(73) Assignee: Teknologian tutkimuskeskus VTT Oy (FI)

( * ) Notice: Subject to any disclaimer, the term of this patent is extended or adjusted under 35 U.S.C. 154(b) by 0 days.

(21) Appl. No.: 14/128,634

(22) PCT Filed: Jun. 29, 2012

(86) PCT No.: PCT/FI2012/050688
§ 371 (c)(1),
(2), (4) Date: Jan. 29, 2014

(87) PCT Pub. No.: WO2013/004906
PCT Pub. Date: Jan. 10, 2013

(65) Prior Publication Data
US 2014/0212926 A1   Jul. 31, 2014

(30) Foreign Application Priority Data

Jul. 1, 2011   (FI) .................................... 20115704

(51) Int. Cl.
*C12P 21/00* (2006.01)
*C07K 14/00* (2006.01)
*C07K 14/37* (2006.01)
*C12N 15/67* (2006.01)

(52) U.S. Cl.
CPC ................ *C12P 21/00* (2013.01); *C07K 14/00* (2013.01); *C07K 14/37* (2013.01); *C12N 15/67* (2013.01); *C07K 2319/70* (2013.01)

(58) Field of Classification Search
None
See application file for complete search history.

(56) References Cited

U.S. PATENT DOCUMENTS

| 7,060,669 B1 | 6/2006 | Penttila et al. |
| 7,335,492 B2 | 2/2008 | Penttila et al. |
| 2003/0059910 A1 | 3/2003 | Moloney et al. |
| 2004/0005660 A1 | 1/2004 | Ludevid Mugica et al. |
| 2006/0106120 A1 | 5/2006 | Abe et al. |
| 2006/0121573 A1 | 6/2006 | Torrent et al. |
| 2006/0160180 A1 | 7/2006 | Drapeau et al. |
| 2009/0233110 A1 | 9/2009 | Seyffer et al. |

OTHER PUBLICATIONS

Conley. Et al.; Protein body-inducing fusions for high-level production and purification of recombinant proteins in plants; Plant Biotechnology Journal; May 2011; pp. 419-433; vol. 9; Society for Experimental Biology, Association of Applied Biologist and Blackwell Publishing Ltd.
Joensuu, et al.; Hydrophobin Fusions for High-Level Transient Proein Expression and Purification in *Nicotiana benthamiana*; Plant Physiology; Feb. 2010; pp. 622-633; vol. 152; American Society of Plant Biologists.
Lahtinen, et al.; Hydrophobin (HFBI): A potential fusion partner for one-step purification of recombinant proteins from insect cells; Protein Expression and Purification; Jan. 11, 2008; pp. 18-24; vol. 59; Elsevier Inc.
Mustalahti, et al.; Intracellular protein production in *Trichoderma reesei* (*Hypocrea jecorina*) with hydrophobin fusion technology; New Biotechnology; Sep. 2011; 7 pages; vol. 00 No. 00; Elsevier.
Torrent, et al.; Eukaryotic protein production in designed storage organelles; BMC Biology; Jan. 28, 2009; 14 pages; vol. 7, No. 5; BioMed Central.
Bellucci, et al.; Zeolin is a recombinant storage protein with different solubility and stability properties according to its localization in the endoplasmic reticulum or in the chloroplast; Journal of Biotechnology; Aug. 31, 2007; pp. 97-105; vol. 131, No. 2; Elsevier Science BV, Amsterdam.
Benchabane, et al.; Preventing unintended proteolysis in plant protein biofactories; Plant Biotechnology Journal; Mar. 21, 2008; pp. 633-648; vol. 6; Blackwell Publishing Ltd.
Galili; ER-derived compartments are formed by highly regulated processes and have special functions in plants; Plant Physiology; Nov. 2004; pp. 3411-3413; vol. 136; American Society of Plant Biologists.
Linder, et al.; Efficient purification of recombinant proteins using hydrophobins as tags in surfactant-based two-phase systems; Biochemistry; Aug. 26, 2004; pp. 11873-11882; vol. 43; ACS Publications.
Saito, et al.; A green fluorescent protein fused to rice prolomin forms protein body-like structures in transgenic rice; Journal of Experimental Botany; Feb. 2009; pp. 615-627; vol. 60 No. 2; Oxford Jounrals.

*Primary Examiner* — Suzanne M Noakes

(57) ABSTRACT

The present invention concerns a method for improving the expression levels of proteins, wherein hydrophobin fusion proteins are expressed, thereby inducing the formation of protein bodies, and wherein said hydrophobin fusions are co-expressed with a target protein or with a further fusion of the target protein.

10 Claims, 1 Drawing Sheet

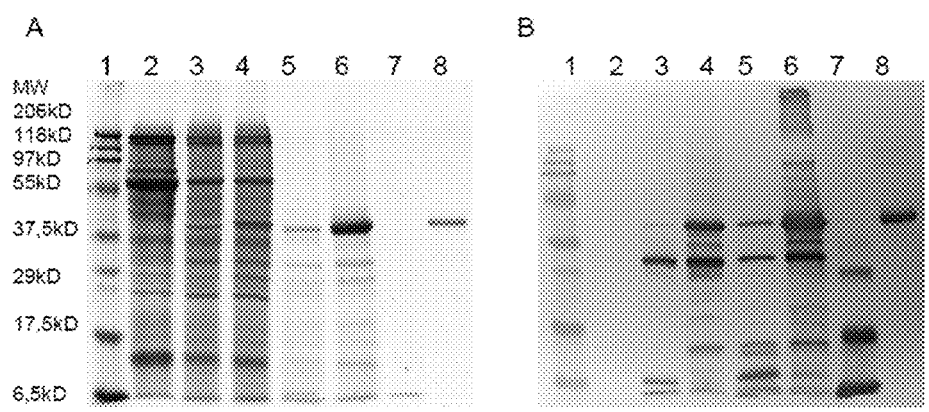

IMPROVING THE PRODUCTION OF FOREIGN PROTEINS

FIELD OF THE INVENTION

The present invention concerns a method for improving the expression levels of various target proteins, by utilizing the co-expression of these target proteins with well-expressing hydrophobin fusion proteins, thereby inducing the formation of protein bodies, which are suitable for the storage of the expression products.

DESCRIPTION OF RELATED ART

The use of recombinant proteins as medicaments and for industrial processes is increasing rapidly, and will continue to increase in the future. Low production levels limit the commercial production of many valuable industrial and medicinal proteins. Foreign proteins can be vulnerable to the degradative action of both intracellular and extracellular proteases, and other production conditions. Correspondingly, the produced proteins are often harmful for the metabolism and growth of the host cell. A wide range of host cell systems have been developed in the past. An example is plant cells, which have the advantage of being considered safe and inexpensive.

Fusion proteins have been developed for various functions, generally to increase the accumulation of recombinant proteins in heterologous expression systems, to assist in their subsequent purification, or to follow the movements of a protein in a living cell. If the fusion tag alters the activity of the target protein, removal of said tag might be required later on. In plants, studies have shown that expressing recombinant proteins as fusions may have a positive impact on their accumulation (Benchabane et al. 2008, Preventing unintended proteolysis in plant protein bio factories. *Plant Biotechnol J* 6, 633-648). The fusions can be accomplished using known genetic engineering techniques. The use of hydrophobin fusions to improve expression levels has been shown by Joensuu and colleagues (Hydrophobin fusions for high-level transient protein expression and purification in *Nicotiana benthamiana. Plant Physiology*, 2010, vol. 152, pp. 622-633). Seeds have the advantage of being able to produce and store high yields of protein in a stable, compact environment for long periods of time. Storage proteins can be stored in specialized endoplasmic reticulum (ER)-derived compartments in developing seeds (Galili 2004, ER-derived compartments are formed by highly regulated processes and have special functions in plants. *Plant Physiol* 136, 3411-3413). Protein bodies are ER-derived organelles that stably accumulate large amounts of storage proteins in seeds. They are highly mobile and exhibit varying dynamic patterns of movement throughout the cells, dependent on intact actin microfilaments and a functional actomyosin motility system. In nature, protein bodies generally form directly within the lumen of the ER, where they can remain permanently stored. After formation, they can alternatively bud off from the ER as discrete spherical organelles, where they can either reside in the cytosol or can be sequestered into protein storage vacuoles by autophagy. In these membrane-covered protein bodies, the storage proteins can remain stable for long periods of time.

The phenomenon of protein body formation is also known when using a fraction of the gamma-zein protein of corn, i.e. the zera domain (see e.g. Bellucci et al. Zeolin is a recombinant storage protein with different solubility and stability properties according to its localization in the endoplasmic reticulum or in the chloroplast. *Journal of Biotechnology*, 2007, 131(2), 97-105). Zeolin and the ELP protein (elastin-like polypeptide) have both been shown to induce the formation of protein bodies, for example in tobacco leaves. But in these areas, no co-expression has been attempted to cause the desired improvements. Further, hydrophobin, zera and ELP do not have similarities on a sequence level, and are also not related on an evolutionary scale. Another developed fusion method specific to plants is the use of an oleosin fusion for the accumulation of fusion proteins in seed oil bodies (U.S. Pat. No. 7,332,587).

It has also been demonstrated that this protein body formation is not limited to plant cells, but can also be induced in other eukaryotic cells (e.g. insect, mammalian, and fungal cells) (see e.g. U.S. Pat. No. 7,575,898; US 20060121573; Saito Y. et al, A green fluorescent protein fused to rice prolamin forms protein body-like structures in transgenic rice. *J. Exp. Bot.*, 2009, 60, 615-627; and Torrent M et al, Eukaryotic protein production in designed storage organelles, *BMC Biol.*, 2009, 7, 5). Although the induction of the protein bodies has previously been demonstrated to increase the expression level of the fused target protein and simplify its purification, co-expression has not been previously described. Thus, there is still a need for methods specifically designed for the production of hard-to-express target proteins that are potentially harmful to the host cell, and particularly for methods providing high expression levels.

SUMMARY OF THE INVENTION

It is an aim of the present invention to provide a method for improving the expression levels of target proteins.

Particularly, it is an aim of the present invention to provide a method, with such improved expression levels, that it can be used for a wide range of target proteins.

These and other objects, together with the advantages thereof over known methods, are achieved by the present invention, as hereinafter described and claimed.

The idea behind the present invention is a co-expression technique, i.e. the improvement of heterologous protein expression by simultaneously expressing it with the well-accumulating hydrophobin fusion protein. This has been found to improve the yield of the heterologous target protein. This heterologous product has been found to localize in membrane-covered protein bodies, which resemble the storage protein bodies found in seeds. The protein bodies protect the target protein from proteases and simultaneously protect the host cells from potential adverse effects of the protein.

Thus, the present invention concerns a method for improving the expression levels of target proteins by co-expressing them with hydrophobin fusion proteins, which induce the formation of protein bodies.

More specifically, the method of the present invention is characterized by what is stated in the claims.

Further, the uses according to the present invention are characterized by what is stated in the claims.

Considerable advantages are obtained by means of the invention. Protein body formation enables high local concentrations of heterologous proteins to exist within the limited space of the cell, while insulating the protein from normal cellular protein degradation mechanisms, and without subjecting the ER to an intolerable level of stress. This enables proteins that are foreign to the cells to be expressed in organelles that protect both the foreign target protein and the cells.

Therefore, the approach used in the present invention provides an effective strategy for enhancing the production yield of recombinant proteins via accumulation in stable protein body organelles, while also providing for an efficient purification strategy.

Using the presently described technique, the expression levels of the target protein can be increased in the protein bodies using co-expression of the target protein without fusion, i.e. by only using fusion technology on the easy-to-express protein. Alternatively, the target protein can also be expressed as a hydrophobin fusion, whereby the storage into the protein bodies becomes more effective, and the other part of the fusion can be used to simplify the protein purification.

When, for example, GFP is expressed as a fusion with HFBI, the infiltrated leaves remain fairly healthy (Joensuu et al. 2010). Therefore, GFP-HFBI accumulation continues to increase relative to the endogenous plant proteins, allowing for simpler downstream purification processes. The tissue-protective effect is considered to be due to the accumulation of the fusion protein in protein bodies.

Thus, the protein bodies induced by the hydrophobin fusions protect: i) the foreign proteins from premature degradation, and ii) the cells from the foreign proteins to be expressed.

Next, the invention will be described more closely with reference to the attached drawing and a detailed description.

BRIEF DESCRIPTION OF THE DRAWING

FIG. 1 shows images of the SDS-PAGE (A) and Western blot (B) analyses illustrating the expression of an exemplary target protein fusion, ProteinA-HFBI, alone and as co-expression with an exemplary easy-to-express fusion, GFP-HFBI in N. benthamiana, with the lanes showing the following: 1. size marker, 2. wt, 3. ProteinA-HFBI tsp, 4. ProteinA-HFBI-GFP-HFBI tsp, 5. ProteinA-HFBI upper phase, 6. ProteinA-HFBI—GFP-HFBI upper phase, 7. Ctrl HFBI 400 ng, 8. Ctrl GFP-HFBI 1 µg (with 10 µl of protein extract loaded per lane, unless otherwise specified).

DETAILED DESCRIPTION OF THE PREFERRED EMBODIMENTS OF THE INVENTION

The present invention concerns a method for improving the expression levels of target proteins, wherein hydrophobin fusion proteins are expressed intracellularly, thereby inducing the formation of protein bodies. Particularly, the method includes co-expressing the hydrophobin fusion protein with a target protein or with a further fusion of the target protein, thus providing improved protein production.

By "fusion protein", or by the simpler term "fusion", is meant a fusion of at least two parts obtained from separate proteins into a single molecule. Thus, a hydrophobin fusion protein is a combination of a type of hydrophobin with another protein or protein part. Similarly, a fusion of a target protein is a combination of the target protein with another protein or protein part. Generally, the "other" protein or protein part of the fusion is selected from those that provide an increase in the accumulation of the "main" protein (i.e. the target protein) in the used expression system, from those assisting in the subsequent protein purification, or from those providing simple detection. The "other" protein can be, for example, GFP, which is both easy to express and easy to detect.

By "improved protein production" is meant protein production which is at least 3%, preferably at least 5%, more preferably at least 10%, particularly at least 20%, and most suitably at least 30% better than protein production without co-expression.

Thus, the present invention is an improvement of the expression of hard-to-express heterologous target proteins by simultaneously expressing an easy-to-express fusion protein. This fusion protein can be formed, for example from GFP fused to a hydrophobin protein.

The target protein may be any protein, particularly any heterologous protein, originating from bacteria or higher or lower eukaryotes.

By "recombinant proteins" are meant here proteins that are not natural products of an organism.

DNA sequences encoding the desired homologous or heterologous proteins may be transferred by a suitable method to a host. By "heterologous protein" is meant a protein produced by another organism species. Correspondingly, by "homologous protein" is meant a protein produced by the same organism species.

The expression may comprise the steps of selecting a gene encoding the target protein, and expressing the desired target protein in a host.

Further, the method of the invention may comprise the steps of cultivating said host in a suitable culture medium, and expressing the target protein in said cultivated host.

"A host" denotes here any protein production host selected or genetically modified to produce efficiently a desired product and being useful for protein production for e.g. analytical, medical or industrial use.

Although the expressed target proteins may be secreted from the host, according to the present invention they are most suitably left in the endoplasmic reticulum until use.

By "secretable protein" or "secreted protein" is meant here a protein that is secreted outside of the host cell.

The protein fusions of the invention include fusions with one or more types of hydrophobins.

The hydrophobin fusion protein is preferably a fusion of hydrophobin to any easy-to-express protein, which particularly is selected from easy-to-express proteins functioning as tags, dyes or labels, such as Green Fluorescent Protein (GFP).

Hydrophobins are dipolar proteins produced by filamentous fungi to better adapt to their environment. In nature, hydrophobins are secreted from the cells, thus allowing, among others, the fungal filaments to attach to or grow on water/air surfaces. They can also remain intracellular. Overexpression of hydrophobins (targeted to the inside of the endoplasmic reticulum) leads to the formation of synthetic membrane-covered protein bodies.

The biological function of hydrophobins is involved in the adaptation of fungi to their environment by controlling interfacial forces. A distinct structural feature of hydrophobins is that one part of the surface of the structure is occupied by hydrophobic aliphatic side chains forming an exposed hydrophobic patch on one end of the protein. This is notable since hydrophobic side chains are usually buried in the core, therefore stabilizing the protein fold. The amphiphatic appearance of hydrophobins closely resembles the common structure and behavior of surface-active molecules with one hydrophobic and one hydrophilic part. Because of these properties, hydrophobins are capable of self-assembling into an amphiphatic protein membrane at hydrophilic-hydrophobic interfaces.

Due to their unique surface active properties, hydrophobins are also capable of altering the hydrophobicity of their respective fusion partner, thus enabling efficient purification using a surfactant-based aqueous two-phase system (ATPS) (Linder M B, et al. Efficient purification of recombinant proteins using hydrophobins as tags in surfactant-based two-phase systems. *Biochemistry* 2004, 43, 11873-11882, and U.S. Pat. No. 7,335,491). These features also make the hydrophobins particularly useful in the present invention.

In the context of the present invention, the term "hydrophobin" is intended to include all polypeptides belonging to the classes of hydrophobins, including HFBI, HFBII, HFBIII, SRHI, SC3, HGFI and other polypeptides that have resemblance in properties or sequence to said polypeptides.

According to an embodiment of the invention, the hydrophobins include polypeptides comprising amino acid sequences, which have at least 40% similarity at the amino acid sequence level to the mentioned HFBI, HFBII, HFBIII, SRHI, SC3 and HGFI. The level of similarity can of course be also higher, preferably at least 50%, more preferably at least 60%, particularly at least 80%, and most suitably at least 90%.

The hydrophobins used in the present invention are synthesized on ribosomes associated with the rough ER and then transported into the ER lumen, where they accumulate and assemble into protein bodies. The protein bodies are then transported into the cytoplasm where they remain surrounded by ER membranes and are terminally stored as cytoplasmic organelles. These protein bodies contain proteins with ER-specific glycans as well as other proteins present abundantly in ER, and are surrounded by a distinct membrane studded with ribosomes. Although the distribution pattern of the protein bodies is highly variable, they are most often found clustered together within the cells.

The sources of the hydrophobins suitable for use in the present invention include all filamentous fungi, such as *Trichoderma, Schizophyllum, Aspergillus, Fusarium, Cladosporium*, and *Agaricus* species.

Further, the fungal sources of the present invention invention can be selected more specifically from the group comprising *Aspergillus* spp., *Trichoderma* ssp., *Neurospora* spp., *Fusarium* ssp., *Penicillium* ssp., *Humicola* ssp., *Tolypocladium geodes, Schwanniomyces* ssp., *Arxula*, ssp., *Trichosporon* ssp., *Kluyveromyces* ssp., *Pichia* ssp., *Hansenula* ssp., *Candida* spp., *Yarrowia* ssp., *Schizosaccharomyces* ssp. and *Saccharomyces* ssp.

The presence of a hydrophobin fusion partner does not generally inhibit the function of the target protein. Similarly, e.g. the HFBI fusion has been found not to have a negative impact on the fluorescent properties of GFP. Further, fungal hydrophobins are highly biocompatible since they are a common part of our daily dietary intake and can be used to immobilize target proteins to surfaces, or can be used as carriers to focus enzyme activities to interfaces.

The interesting properties of hydrophobins, such as the unusually strong and specific interaction between polymeric surfactants and these highly soluble hydrophobins, shows promise for use in protein purification from complex intracellular protein extracts. In addition to the hydrophobin fusions, other proteins present in the endoplasmic reticulum also accumulate in the protein bodies. It has now been observed that co-expression of, e.g., a GFP-HFBI fusion improves the expression levels of other foreign proteins simultaneously allocated into the endoplasmic reticulum.

Thus, the easily expressible hydrophobin fusion protein (as an example: GFP-HFBI) induces the formation of membrane-covered protein bodies, when allocated to the endoplasmic reticulum. If another target protein is simultaneously overexpressed into the endoplasmic reticulum, also this protein is accumulated into the protein bodies. If desired, these target proteins can be separated from each other after their expression by using conventional purification strategies. In the protein bodies, the target proteins are protected from the proteases of the cells. Further, the protein bodies protect the host cell from potential adverse effects of the expressed protein(s).

The target protein can be co-expressed together with said hydrophobin fusion into the endoplasmic reticulum: i) as such, or ii) also as a hydrophobin fusion. In the latter case, the accumulation of protein into the protein bodies is more effective, due to the interactions of the GFP-HFBI and the hydrophobin parts of the target protein. Alternatively, the target protein can be fused genetically to form a part of an easily expressible hydrophobin fusion protein. Further, the hydrophobin part linked to the target protein can be utilized in protein purification.

The technique of improving the expression of proteins in various eukaryotic hosts is a valuable technique, particularly when expressing problematic target proteins, the expression of which is difficult using commonly known techniques. If said proteins are fused with hydrophobin, the properties of the hydrophobin can be utilized in protein purification.

Thus, the method of the present invention can be used, for example, for purification, for targeting proteins to specific surfaces, for manufacturing biosensors and for targeting enzyme activity.

The following example illustrates the function of the above described fusions and their co-expression, as provided by the present invention, and is not intended to limit the scope of the invention.

EXAMPLE

Protein Fusions

In this example, SDS-PAGE and Western blot analyses were carried out on a ProteinA-HFBI fusion, expressed alone, as well as on a co-expression of this fusion (ProteinA-HFBI) with GFP-HFBI (as an easy-to-express fusion protein) in *N. benthamiana*. In the analyses, 10 µl of protein extract was loaded per lane.

FIG. 1 shows the results of the analyses, with the lanes showing the following:
1. size marker,
2. wt,
3. ProteinA-HFBI tsp,
4. ProteinA-HFBI—GFP-HFBI tsp,
5. ProteinA-HFBI upper phase,
6. ProteinA-HFBI—GFP-HFBI upper phase,
7. control HFBI 400 ng, and
8. control GFP-HFBI 1 µg.

The invention claimed is:

1. A method for improving expression levels of target proteins, comprising; expressing intracellularly in eukaryotic host cells hydrophobin fusion proteins, thereby inducing formation of protein bodies, and co-expressing the hydrophobin fusion protein with a target protein or with a further fusion of the target protein within said protein bodies.

2. The method according to claim 1, wherein the expression and the formation of the protein bodies takes place in an endoplasmic reticulum of the host cells.

3. The method of claim 1, wherein the host cells are selected from plant cells, or from insect, mammalian, yeast, or fungal cells.

4. The method of claim 1, wherein the hydrophobin is acquired from a filamentous fungi, and selected from the group consisting of HFBI, HFBII, HFBIII, SRHI, SC3, and HGFI.

5. The method of claim 1, wherein the hydrophobin fusion protein is a fusion protein with a hydrophobin and Green Fluorescent Protein (GFP).

6. The method of claim 1, wherein the target protein is selected from any heterologous protein, originating from bacteria or higher or lower eukaryotes.

7. The method of claim 1, further comprising, forming a fusion of the target protein before co-expression.

8. The method of claim 7, further comprising forming a fusion of the target protein with GFP before co-expression.

9. The method of claim 1, further comprising storing the expressed protein products in the host cells prior to optional subsequent use.

10. The method of claim 1, wherein the hydrophobin is acquired from a filamentous fungi, and comprises a polypeptide comprising an amino acid sequence having at least 40% similarity at the amino acid sequence level to one of HFBI, HFBII, HFBIII, SRHI, SC3, or HGFI.

* * * * *